United States Patent [19]

Haefliger, deceased

[11] Patent Number: 5,075,318

[45] Date of Patent: Dec. 24, 1991

[54] 8α-ACYLAMINOERGOLINE, ITS PREPARATION AND PHARMACEUTICAL COMPOSITIONS CONTAINING IT

[75] Inventor: Walter Haefliger, deceased, late of Langnau, Switzerland, by Irma C. Haefliger, legal representative

[73] Assignee: Sandoz Ltd., Basel, Switzerland

[21] Appl. No.: 608,454

[22] Filed: Nov. 2, 1990

Related U.S. Application Data

[63] Continuation of Ser. No. 482,430, Feb. 20, 1990, abandoned, which is a continuation of Ser. No. 370,360, Jun. 22, 1989, abandoned, which is a continuation of Ser. No. 209,748, Jun. 21, 1988, abandoned.

[30] Foreign Application Priority Data

Jun. 23, 1987 [DE] Fed. Rep. of Germany ....... 3720656

[51] Int. Cl.$^5$ .................... A61K 31/44; C07D 457/12
[52] U.S. Cl. ........................................ 514/288; 546/68
[58] Field of Search ........................... 546/68; 514/288

[56] References Cited

PUBLICATIONS

Haefliger, CA104-130106r (1986).
Haefliger, CA111-78483q (1989).

*Primary Examiner*—Cecilia Shen
*Attorney, Agent, or Firm*—Gerald D. Sharkin; Robert S. Honor; Thomas O. McGovern

[57] ABSTRACT

8α-Acylaminoergoline useful in the treatment of psychotic disorders and Parkinson's disease.

5 Claims, No Drawings

8α-ACYLAMINOERGOLINE, ITS PREPARATION AND PHARMACEUTICAL COMPOSITIONS CONTAINING IT

This is a continuation of application Ser. No. 07/482,430, filed Feb. 20, 1990 now abandoned, which in turn is a continuation of application Ser. No. 07/370,360, filed June 22, 1989, now abandoned, which in turn is a continuation of application Ser. No. 07/209,748, filed June 21, 1988, now abandoned.

This invention relates to 8α-acylaminoergoline, a process for its production, pharmaceutical compositions containing it and its use as a pharmaceutical.

UK-Patent Specification 2 152 507 describes a broad class of substituted 8α-acylaminoergolines which posses prolactin secretion inhibiting, luteinising hormone secretion inhibiting and apomorphine antagonistic activities.

It has now surprisingly been found that one compound of this class, which has not up until now been specifically disclosed, has particularly valuable pharmacological properties. In particular, the compound has a surprisingly potent and long-lasting neuroleptic activity and is well tolerated e.g. a surprisingly low propensity to induce extrapyramidal and endocrine side effects as indicated in the pharmacological tests described hereinafter.

The present invention according provides N-[5R,8S,10R)-2,6-di-methyl-ergoline-8-yl]-2-ethyl-2-methyl-butanamide of formula I,

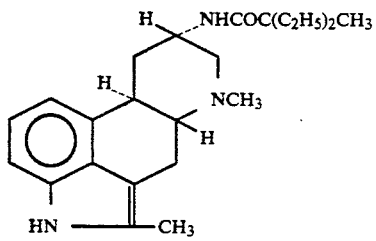

in free base form or in acid addition salt form.

The invention also provides a process of producing the compound of formula I by reacting 8α-amino-2,6-dimethylergoline of formula II,

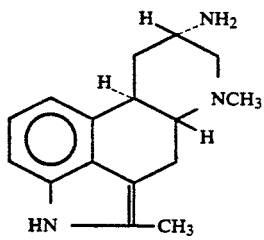

with the compound of formula III,

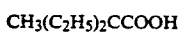

CH$_3$(C$_2$H$_5$)$_2$CCOOH    III or a reactive derivative thereof and recovering the resultant compound of formula I in free base form or in acid addition salt form.

The process can be carried out in conventional manner. Suitable reactive derivatives of the compound of formula III include e.g. acid halides, in particular the acid chloride, or the imidazolide. Reaction with acid halides suitably may be effected in the presence of a base, such as triethylamine or Hünig-base in an inert solvent such as methylene chloride. Reaction with the imidazolide (obtained e.g. by reaction of the compound of formula III with N,N-carbonyldiimidazole) suitably may be carried out in an inert solvent, such as tetrahydrofuran or ethanol, e.g. at reflux temperature. Where the compound of formula III is employed as such, reaction may suitably be effected in the presence of propanephosphonic acid anhydride.

The starting compound of formula II is described in UK-Patent Specification 2 152 507.

The compound of formula I may be obtained in free base form or in acid addition salt form, e.g. in the form of its pharmaceutically acceptable acid addition salts. The free base form of the compound of formula I may be converted into acid addition salt forms in conventional manner and vice versa. Suitable pharmaceutically acceptable acid addition salts include both such salts with inorganic acids, for example, the hydrochloride, as well as such salts with organic acids, for example the oxalate or hydrogen maleate. The hydrogen maleate is the preferred salt.

The compound of formula I exhibits pharmacological activity and is, therefore, useful as a pharmaceutical. In particular, the compound of formula I shows potent and long lasting neuroleptic activity as can be demonstrated in the following tests:

The compound of formula I inhibits apomorphine induced gnawing in the rat in a method based on that of P.A. Janssen et al., Arzneim.-Forsch. (Drug Res.) 10, 1003–1005 (1960):

Groups of 3–6 rats (males and females, 90–160 g, Sprague-Dawley, Süddeutsche Tierfarm, Tuttlingen, West Germany) are treated with the test-drug orally and after a pre-determined time further treated with 2.0 mg/kg i.v. apomorphine hydrochloride in aq. solution. They are then placed in individual cages lined with corrugated paper. At times 10, 20 and 30 minutes after the apomorphine each rat is observed for 1 minute. If gnawing occurred during an observation period, that observation is scored as positive. Thus, three scores are obtained from each rat. The supra-maximal dose of apomorphine invariably produces gnawing in all controls at all observation times. Out of the total number of observations per treatment group, the number of positives is noted. The dose of drug which causes a 100% inhibition of the apomorphine induced gnawing is taken as the threshold dose. After a pretreatment time of 3 hours the threshold dose for the compound of formula I is 0.2 mg/kg p.o., after a pretreatment time of 6 hours also 0.2 mg/kg p.o.

Furthermore the compound of formula I binds to dopamine receptors as characterised by the displacement of $^3$H-ligands from their respective binding sites in the homogenates of brain tissue.

The affinity to D-1 receptor sites [cf. W. Billard et al., Life Sci. 35, 1885–1893 (1984)] using $^3$H-(R)-(+)-8-chloro-7-hydroxy-3-methyl-5-phenyl-2,3,4,5-tetrahydro-1H-3-benzazepine ($^3$H-SCH 23390) as ligand is determined as follows:

Fresh calf brain striatal tissue is homogenized in a 20 fold volume of Tris-HCl buffer (50 mM, pH 7.4 at 25° C.) using a Polytron tissue homogenizer. The homogenate is centrifuged for 10 minutes at 50,000 g (4° C.) and the supernatant discarded. The pellets are resuspended in the same buffer as before. The suspension is incubated for 20 minutes at 37° C. and then recentrifuged as before. The resulting pellets are stored frozen at −20° until their use in the binding assay. For the binding assay the pellets are resuspended in Tris-HCl buffer (50 mM, pH 7.4 at 37° C., containing 120 mM NaCl) in such a way that the final volume of 2 ml contains membranes corresponding to approximately 5 mg original tissue weight. $^3$H-SCH 23390 is added to give a final concentration of 0.1 nM. The assays for the determination of nonspecific binding additionally contain 1 μM unlabelled SCH 23390. The test compound is added to give 5 to 9 different concentrations. The assays are incubated for 50 minutes at 37° C. followed by vacuum filtration through Whatman GF/B filters. The filters are rinsed twice with 5 ml of ice cold Tris-HCl buffer. The filters are monitored for radioactivity through liquid scintillation counting. The IC$_{50}$ value (i.e. the concentration of the test drug which inhibits specific binding of $^3$H-SCH 23390 by 50%) is determined by linear regression analysis from the Hill plots. The IC$_{50}$ of the compound of formula I is about 50 nM.

The high affinity of the compound for D-2 receptor sites may be determined in the $^3$H-spiperone binding assay [cf. S. Urwyler & D. Coward, Naunyn-Schmiedeberg's Arch. Pharmacol. 335, 115–122 (1987)]. Calf striatal membranes are prepared as described above for the $^3$H-SCH 23390 binding experiments. The pellets are resuspended in 50 mM Tris-HCl buffer (pH 7.7), containing 120 mM NaCl, to give a membrane concentration corresponding to 4 mg of original tissue weight per 4 ml assay volume. 0.5 μM Cinanserin is added to prevent the binding of $^3$H-spiperone to 5HT$_2$-receptors. The concentration of $^3$H-spiperone is 0.1 nM; the samples for the measurement of non-specific binding additionally receive 5 μM haloperidol. The samples are incubated for 40 minutes at room temperature, followed by filtration and liquid scintillation counting as described above. The compound of formula I has an IC$_{50}$ of about 20 nM.

The compound of formula I is well tolerated in mice up to 100 mg/kg p.o. The non-toxic dose level in the dog after a 4 week treatment is 3 mg/kg/day p.o.

A typical undesirable side effect of most neuroleptics on endocrine functions is an increased prolactin release.

The compound of formula I influences serum prolactin levels in rats only at high doses (≧10 mg/kg) as demonstrated in the following test method upon subcutaneous administration [cf. E. Flückiger et al., Experientia 34, 1330–1331 (1978)]:

Male OFA-rats of about 250 g body weight are brought to the experimental room 24 hours before the actual experiment. They are kept in appropriate cages by tens. After the experimental treatment they are kept singly. Food and water are freely available. Various doses of the compound or the vehicle are administered s.c. to groups of 5 animals. In this standard experiment the animals are decapitated 4 hours after treatment. The sera of the individual animals are deep frozen until assayed. Prolactin is then measured in aliquots by radioimmunoassay. The serum prolactin levels are expressed in ng/ml in terms of the prolactin standard NIAMD-RPrl-RP1. After subcutaneous administration of 10 mg/kg of the compound of formula I only a moderate increase of serum prolactin levels in male rats occurrs 4 hours after administration.

Oral administration of the compound also produces only weak effects on prolactin levels. The test is performed as follows:

Male rats (120–140 g, Sprague-Dawley, Süddeutsche Tierfarm, Tuttlingen, West Germany) are maintained on a 12:12 light dark cycle (lights on 06.00, off 18.00 hrs). On the evening before the experiment, animals are marked for identification purposes and caged in groups of 4 into makrolon (type 3) cages. The next morning, the rats in each group receive 10 mg/kg p.o. of the test drug or placebo (normal saline solution+2 drops HCl) 2, 4, 8, 16 or 24 hours before they are killed by decapitation. Blood samples are collected in plastic tubes, centrifuged to obtain the serum, which is then stored at −20° C. until assayed for prolactin. Prolactin in the serum is measured by radioimmunoassay according to that of A. Häusler et al., J. Ultrastruct. Res. 64, 74 (1978). The compound of formula I significantly decreases serum prolactin levels between 4 and 8 hours after administration of 10 mg/kg p.o. After 16 hours, a significant increase occurrs, which later declines (24 hours) towards normal.

The weak effect on serum prolactin levels reduces the likehood of undesirable endocrine side effects, e.g. galactorrhea or gynecomastia.

Moreover, the compound of formula I exhibits pharmacological properties suggesting a low propensity for inducing extrapyramidal side effects. For instance, the compound has only a weak cataleptogenic activity in the test based upon that of G. Stille et al., Arzneim.-Forsch. (Drug Res.) 21, 252–255 (1971). In this test groups of 4–8 rats (120–170 g, Sprague-Dawley, females and males, Süddeutsche Tierfarm, Tuttlingen, West Germany) receive the test substance orally. At specified times after treatment the catalepsy of each rat is estimated by placing the forepaws on a 7 cm high block. The time for which the animal remains in this unnatural position is measured up to a maximum of 45 seconds. The threshold dose is the final dose, which still causes a catalepsy-median of >10 seconds. The compound of formula I has a threshold dose of 5 mg/kg p.o. determined during an 8 hour measurement period. This is a dose which is at least 25 times higher than that required to antagonize apomorphine induced gnawing.

Additionally, the compound shows dopamine agonist like properties as indicated by the exertion of motor stimulating effects in animals with impaired dopaminergic neurotransmission. For instance, the compound of formula I induces in rats with an unilateral 6-OHDA (6-hydroxydopamine) induced lesion of the substantia nigra [i.e. Ungerstedt rat, c.f. J. M. Vigouret et al. Pharmacology 16 (Suppl. 1), 156–173 (1978)] a long lasting rotational behaviour contralateral to the lesion at relatively low doses (0.5 mg/kg p.o.: 950 rotations within 7 hours).

In view of its high affinity for dopamine D-1 and D-2 receptor sites and its inhibitory effect on apomorphine-induced gnawing and the other tests mentioned above the compound of formula I is useful as a well tolerated neuroleptic e.g. for the treatment of psychotic disorders, such as schizophrenia, psychosis induced by antiparkinson medication or age-related psychiatric disorders frequently associated with dementia (paranoia). Additionally, in view of the results obtained in the Ungerstedt rat the compound of formula I is also useful in the treatment of schizophrenia exhibiting negative symptoms.

For this indication, the appropriate dosage will, of course, vary depending upon, for example, the host, the mode of administration and the nature and severity of the condition being treated. However, in general, satisfactory results in animals are indicated to be obtained at daily dosages from about 0.01 to about 0.6 mg/kg animal body weight. In larger mammals, for example humans, an indicated daily dosage is in the range from about 1 to about 50 mg, preferably from 5 to 40 mg, e.g. 10 to 40 mg of the compound conveniently administered, for example, in divided doses up to four times a day.

In view of the dopamine agonist like activity shown in the Ungerstedt rat test, the compound is further useful in the treatment of Parkinson's disease.

For this indication, the appropriate dosage will, of course, vary depending upon, for example, the host, the mode of administration and the nature and severity of the condition being treated. However, in general, satisfactory results in animals are indicated to be obtained at daily dosages from about 0.1 to about 3 mg/kg animal body weight. In larger mammals, for example humans, an indicated daily dosage is in the range from about 1 to about 50 mg of the compound conveniently administered, for example, in divided doses up to four times a day.

In the above mentioned apomorphine-antagonism test, the compound of formula I has a threshold dose for causing 100% apomorphine inhibition of 0.2 mg/kg p.o. after a pretreatment time of 6 hours, the threshold dose for the known neuroleptic haloperidol being also 0.2 mg/kg p.o. It is, therefore, indicated that the compound of formula I may be administered to larger mammals, for example humans, by similar mode of administration at similar dosages as conventionally employed with haloperidol.

The compound of formula I may be administered in free base form or in pharmaceutically acceptable acid addition salt form. Such salts may be prepared in conventional manner and exhibit the same order of activity as the free base.

The present invention also provides pharmaceutical compositions comprising the compound of formula I in free base or in pharmaceutically acceptable acid addition salt form in association with at least one pharmaceutical carrier or diluent.

The compound of formula I may be administered by any conventional route, in particular enterally, preferably orally, e.g. in the form of tablets or capsules or parenterally, e.g. in the form of injectable solutions or suspensions. For example, for oral administration e.g. in the form of tablets or capsules, the compound of formula I or a pharmaceutically acceptable acid addition salt thereof may be admixed with conventional pharmaceutically acceptable excipients, e.g. inert diluents, such as lactose, mannitol, calcium sulfate, microcristalline cellulose; disintegrating agents, e.g. starch, sodium carboxymethyl cellulose, sodium carboxymethyl starch, alginic acid, crospovidone; binding agents such as cellulose derivatives (methyl-, hydroxymethyl-, hydroxypropylmethyl-), povidone, gelatine; lubricating agents e.g. siliciumdioxide, stearic acid, magnesium or calcium stearate; hydrogenated oils such as castor oil, glycerolesters e.g. palmitostearate and/or flavouring, colouring and sweetening agents. The tablets may be uncoated or coated by known techniques to delay disintegration and absorption in the gastrointestinal tract and thereby provide a sustained action over a longer period. For parenteral administration suitable sterile aqueous or non-aqueous solutions or suspensions can be employed.

Unit dosage forms contain for example from about 0.25 to about 25 mg of the compound of formula I or a pharmaceutically acceptable acid addition salt thereof.

The pharmaceutical compositions can be prepared according to conventional techniques.

For the manufacture of tablets, the compound of formula I may be mixed with lactose and granulated with water, 0.5% sodium alginate or 5% hydroxypropylmethylcellulose solution. The dried granulate is compressed into tablets in the presence of about 20% of corn starch and 1% of magnesium stearate. In this way, there are obtained, e.g. tablets of the following composition:

| Ingredients | Tablet Weight (mg) |
| --- | --- |
| Compound of formula I hydrogen maleate | 10 |
| Lactose | 100 |
| Corn starch | 30 |
| Hydroxypropylmethylcellulose | 7.5 |
| Magnesium stearate | 1.5 |
| Siliciumdioxide | 1 |
| | 150 |

These tablets, which are provided with a crackline, may be administered orally in a dosage of one half to one tablet 1 to 4 times a day.

Capsules may contain the active agent alone or admixed with an inert solid excipient, for example as mentioned above.

Capsules containing the ingredients indicated below may be prepared by conventional techniques and are administered at a dose of one capsule 1 to 4 times a day.

| Ingredients | Capsule weight (mg) |
| --- | --- |
| Compound of formula I hydrogen maleate | 10 |
| Inert solid excipient (corn, starch, lactose, aerosil, magnesium stearate) | 190 |

Similarly tablets and capsules containing 20 mg of the compound of formula I may be prepared.

The following injectable solution is formulated with the indicated amount of active agent using conventional techniques. The injectable solution is suitable for administration once a day.

| Ingredients | Sterile injectable solution Weight (mg/ml) |
| --- | --- |
| Compound of formula I hydrogen maleate | 5.0 |
| Sodium chloride | 9.0 |
| Ethyl alcohol | 150.0 |
| Sodium hydrogen carbonate to pH 7 | q.s. |
| Water for injection | ad 1 ml |

The solutions may be filtered through a 0.2 μm sterile filter and aseptically filled in ampoules. The ampoules are gassed with carbon dioxide.

The present invention also provides the compound of formula I in free base form or in pharmaceutically acceptable acid addition salt form for use as a pharmaceutical, e.g. for use as a neuroleptic or for use as an antiparkinsonian and, especially for use in any of the specific indications hereinbefore recited in relation to such uses.

The present invention accordingly provides a method for the treatment of psychotic disorders or Parkinson's disease, especially for treating any of the specific conditions hereinbefore recited in relation to such treatment in a subject which comprises administering a therapeutically effective amount of the compound of formula I in free base form or in pharmaceutically acceptable acid addition salt form to a subject in need of such treatment.

The present invention further provides the compound of formula I in free base form or in pharmaceutically acceptable acid addition salt form for use in the manufacture of a pharmaceutical composition for use in the treatment of psychotic disorders or Parkinson's disease.

In the following Example all temperatures are given in degrees centigrade and are uncorrected. The $[\alpha]_D^{20}$ value is also uncorrected.

EXAMPLE

N-[(5R,8S,10R)-2,6-dimethyl-ergoline-8-yl]-2-ethyl-2-methyl-butanamide

A supension of 68 g 2,6-dimethyl-8α-aminoergoline in 1.5 l dichloromethane are pre-cooled to 4° and treated with 78 ml triethylamine. The mixture is treated under stirring dropwise within 25 minutes with 40.5 g 2-methyl-2-ethyl-butyryl chloride. The mixture is stirred for 30 minutes, poured onto 3 l water, the organic phase is dried ($Na_2SO_4$) and concentrated. The residue is chromatographed on 800 g silica gel using dichloromethane/methanol (98:2) to yield the title compound, which is crystallised from diethyl ether, m.p. 191°–192°.

For the preparation of the hydrogen maleate 57.3 g of the base are dissolved in 500 ml ethanol and treated with a solution of 18.09 g maleic acid in 250 ml ethanol. The beginning crystallisation is completed by cooling to 4°. The crystalls are filtered and dried, whereby the hydrogen maleate of the title compound is obtained, m.p. 232°–233°. $[\alpha]_D^{20} = -14.5°$ (c=1.0 in dimethylformamide).

What is claimed is:

1. N-[(5R,8S,10R)-2,6-dimethyl-ergoline-8-yl]-2-ethyl-2-methylbutanamide of formula I,

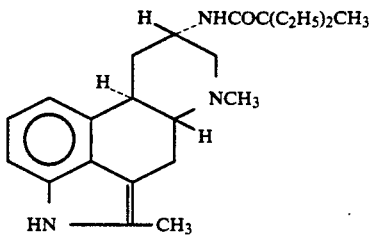

or a pharmaceutically acceptable acid addition salt thereof.

2. The compound of formula I in the form of the hydrogen maleate.

3. A pharmaceutical composition which comprises a therapeutically effective amount of the compound as defined in claim 1 or a pharmaceutically acceptable acid addition salt thereof in association with a pharmaceutical carrier or diluent.

4. A method of treating psychotic disorders, which comprises administering a therapeutically effective amount of the compound of claim 1 or a pharmaceutically acceptable acid addition salt thereof to a subject in need of such treatment.

5. A method of treating Parkinson's disease, which comprises administering a therapeutically effective amount of the compound of claim 1 or a pharmaceutically acceptable acid addition salt thereof to a subject in need of such treatment.

* * * * *